US010448906B2

(12) United States Patent
Lee et al.

(10) Patent No.: US 10,448,906 B2
(45) Date of Patent: Oct. 22, 2019

(54) PORTABLE X-RAY PHOTOGRAPHING DEVICE

(71) Applicants: VATECH Co., Ltd., Gyeonggi-do (KR); VATECH EWOO Holdings Co., Ltd., Gyeonggi-do (KR)

(72) Inventors: Han Sung Lee, Gyeonggi-do (KR); Tae-Woo Kim, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 215 days.

(21) Appl. No.: 15/322,188

(22) PCT Filed: Jul. 3, 2015

(86) PCT No.: PCT/KR2015/006886
§ 371 (c)(1),
(2) Date: Dec. 27, 2016

(87) PCT Pub. No.: WO2016/003241
PCT Pub. Date: Jan. 7, 2016

(65) Prior Publication Data
US 2017/0303874 A1 Oct. 26, 2017

(30) Foreign Application Priority Data
Jul. 3, 2014 (KR) ........................ 10-2014-0083143

(51) Int. Cl.
*G03B 17/54* (2006.01)
*A61B 6/14* (2006.01)
(Continued)

(52) U.S. Cl.
CPC .................. *A61B 6/14* (2013.01); *A61B 6/40* (2013.01); *A61B 6/461* (2013.01); *A61C 19/04* (2013.01);
(Continued)

(58) Field of Classification Search
CPC .. A61B 6/14; A61B 6/145; A61B 6/40; A61B 6/461; A61C 19/04; G03B 17/54;
(Continued)

(56) References Cited

U.S. PATENT DOCUMENTS

2005/0053199 A1    3/2005   Miles
2006/0098779 A1    5/2006   Turner
(Continued)

FOREIGN PATENT DOCUMENTS

| JP | 2006-080875 A | 3/2006 |
|---|---|---|
| JP | 2015-508011 A | 3/2015 |
| KR | 10-2009-0129942 A | 12/2009 |

*Primary Examiner* — Courtney D Thomas
(74) *Attorney, Agent, or Firm* — IP Legal Services, LLC

(57) ABSTRACT

The present invention provides a radiography device for producing an X-ray image of a tooth or a structure supporting the tooth. The radiography device of the present invention includes: an X-ray source for generating X-rays; a projection unit for projecting a user control mode image to the outside as user control information for controlling the X-ray source; and a control unit including an operation unit for user operation, and controlling the X-ray source according to the user control information selected through the operation unit.

8 Claims, 4 Drawing Sheets

(51) Int. Cl.
*A61C 19/04* (2006.01)
*G03B 13/02* (2006.01)
*H04N 5/222* (2006.01)
*H04N 5/232* (2006.01)
*H05G 1/02* (2006.01)
*H05G 1/10* (2006.01)
*A61B 6/00* (2006.01)
*G03B 42/02* (2006.01)
*H04N 5/32* (2006.01)

(52) U.S. Cl.
CPC ............. *G03B 13/02* (2013.01); *G03B 17/54* (2013.01); *G03B 42/02* (2013.01); *H04N 5/222* (2013.01); *H04N 5/232* (2013.01); *H04N 5/32* (2013.01); *H05G 1/02* (2013.01); *H05G 1/10* (2013.01)

(58) Field of Classification Search
CPC ........ G03B 42/02; H04N 5/222; H04N 5/232; H04N 5/32; H05G 1/02; H05G 1/10
USPC ...................................... 378/38–40
See application file for complete search history.

(56) References Cited

U.S. PATENT DOCUMENTS

| | | |
|---|---|---|
| 2007/0230659 A1* | 10/2007 | Turner .................. G03B 42/02 378/63 |
| 2007/0269010 A1 | 11/2007 | Turner |
| 2008/0002046 A1 | 1/2008 | Schumann |
| 2009/0310742 A1 | 12/2009 | Kim et al. |
| 2014/0369459 A1 | 12/2014 | Foos et al. |
| 2018/0140266 A1 | 5/2018 | Foos et al. |
| 2018/0289345 A1 | 10/2018 | Foos et al. |

* cited by examiner

PORTABLE X-RAY PHOTOGRAPHING DEVICE

CROSS REFERENCE TO RELATED APPLICATIONS

This application is a National Stage Patent Application of PCT International Patent Application No. PCT/KR2015/006886 (filed on Jul. 3, 2015) under 35 U.S.C. § 371, which claims priority to Korean Patent Application No. 10-2014-0083143 (filed on Jul. 3, 2014), the teachings of which are incorporated herein in their entireties by reference.

TECHNICAL FIELD

The present invention relates generally to a portable radiography device. More particularly, the present invention relates to a portable radiography device allowing at least one of a user control mode image for controlling the X-ray source, and an intraoral radiograph to be projected to the outside through a projection that has improved visibility, legibility, and convenience.

BACKGROUND ART

In general, a portable radiography device for an intraoral radiograph is used for diagnosing or treating a tooth or a tissue around a tooth.

To perform intraoral radiography, an X-ray sensor, referred as an intraoral sensor, is required in addition to the portable radiography device, wherein in the state where the X-ray sensor is inserted into a mouth, the intraoral radiography is performed by emitting X-rays from the portable radiography device outside the mouth, toward the X-ray sensor, thereby radiographing an oral structure therebetween. Then, the X-ray sensor generates an electric signal, namely, an image signal, based on a dose of X-ray radiation according to a location, and the image signal is displayed through an external display device.

A conventional portable radiography device includes: the X-ray source for generating X-rays; and a control unit for controlling the X-ray source. Recently, there has been introduced a portable radiography device that is integrally provided with a display for displaying user control information of the control unit controlled by a user, namely, a user control mode.

However, considering properties of a portable device, a size of the display should be limited to a predetermined size to be applied to the portable radiography device. Accordingly, the size of the display of the conventional portable radiography device is usually insufficient to display various user control modes, thereby a size of the displayed user control mode is also small, and accordingly, not only is visibility lowered, but also misreading rate increases.

DISCLOSURE

Technical Problem

Accordingly, the present invention has been made keeping in mind the above problems occurring in the related art, and the present invention is intended to propose a portable radiography device provided with a projection unit for projecting at least one of a user control mode image for controlling an X-ray source, and an intraoral radiograph to the outside, thereby it is possible to improve visibility and legibility of user control information or the user control mode image, and the intraoral radiograph, and also it is possible to reduce the size and improve portability of the portable radiography device by replacing the conventional fixed-type display device.

Technical Solution

In order to achieve the above object, according to one aspect of the present invention, there is provided a portable radiography device including: an X-ray source for generating X-rays; a projection unit for projecting at least one of a user control mode image including user control information for controlling the X-ray source, and an intraoral radiograph obtained through an intraoral sensor, to the outside; and a control unit including an operation unit for user operation, and controlling the X-ray source according to the user control information selected through the operation unit, or allowing the intraoral radiograph to be projected to the outside through the projection unit.

Here, the user control information may include at least one of a patient, an object, a form of X-ray imaging, a tube voltage, a tube current, and an X-ray exposure time.

Further, the projection unit may include a projecting device using one of liquid crystal display (LCD) projection, liquid crystal on silicon (LCOS) projection, and digital light processing (DLP) projection.

The portable radiography device may further include: a housing for accommodating the X-ray source and the control unit therein; and an X-ray radiating guide provided in the housing, and radiating the X-rays, wherein the projection unit and the operation unit are respectively provided on a side of the housing or a side of the X-ray radiating guide.

Further, the X-ray radiating guide may be rotatable relative to the housing.

Further, the projection unit may be movable or rotatable along the side of the X-ray radiating guide.

Further, the operation unit may include at least one of a control button and a jog dial.

The portable radiography device may further include a communication unit for receiving an image signal from the intraoral sensor wirelessly or by wire, such that the projection unit projects the intraoral radiograph obtained from the image signal to the outside.

Advantageous Effects

According to the present invention having the above-described characteristics, a portable radiography device is advantageous in that since there is provided a projection unit for projecting at least one of a user control mode image for controlling an X-ray source, and an intraoral radiograph to the outside, it is possible to improve visibility and legibility of user control information or the intraoral radiograph, and also it is possible to display the user control mode image or the intraoral radiograph on any area through a projection that is detachable from a desired location, such as a wall, a ceiling, a screen, or the like, and is movable. Thereby, while watching the enlarged user control mode image projected and displayed at a desired location, the user can select and change the user control mode, and can perform radiography according to the selected user control mode, or it is possible for the user to diagnose and counsel a patient while watching the enlarged intraoral radiograph projected and displayed at a desired location.

The portable radiography device according to the present invention is further advantageous in that since an additional display is detachable, it is possible to reduce the size thereof, thereby improving portability.

DESCRIPTION OF REFERENCE CHARACTERS OF IMPORTANT PARTS

100: X-ray source
200: control unit
300: projection unit
400: housing
500: X-ray radiating guide

MODE FOR INVENTION

Reference will now be made in greater detail to exemplary embodiments of the present invention, an example of which is illustrated in the accompanying drawings. The present invention may be embodied in many different forms without departing from the spirit and significant characteristics of the invention. Therefore, the embodiments of the present invention are disclosed only for illustrative purposes and should not be construed as limiting the present invention.

Figure 1:
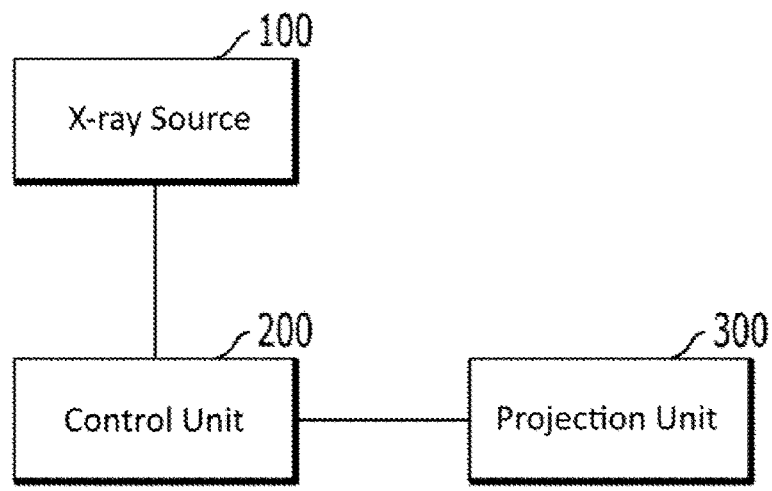
FIG. 1 is a block diagram illustrating a configuration of a portable radiography device of the present invention.

FIG. 1 is a block diagram illustrating a configuration of a portable radiography device of the present invention.

Referring to FIG. 1, the portable radiography device of the present invention includes: an X-ray source 100; a control unit 200 controlling a motion of the X-ray source 100; and a projection unit 300 projecting a user control mode image of the control unit 200 to the outside.

The X-ray source 100 serves to generate X-rays for producing an X-ray image of a tooth or a tissue around a tooth. For example, the X-ray source may be a field emission X-ray source with a nanostructure. A specific configuration of the X-ray source 100 will be described, with reference to FIG. 2.

Figure 2:
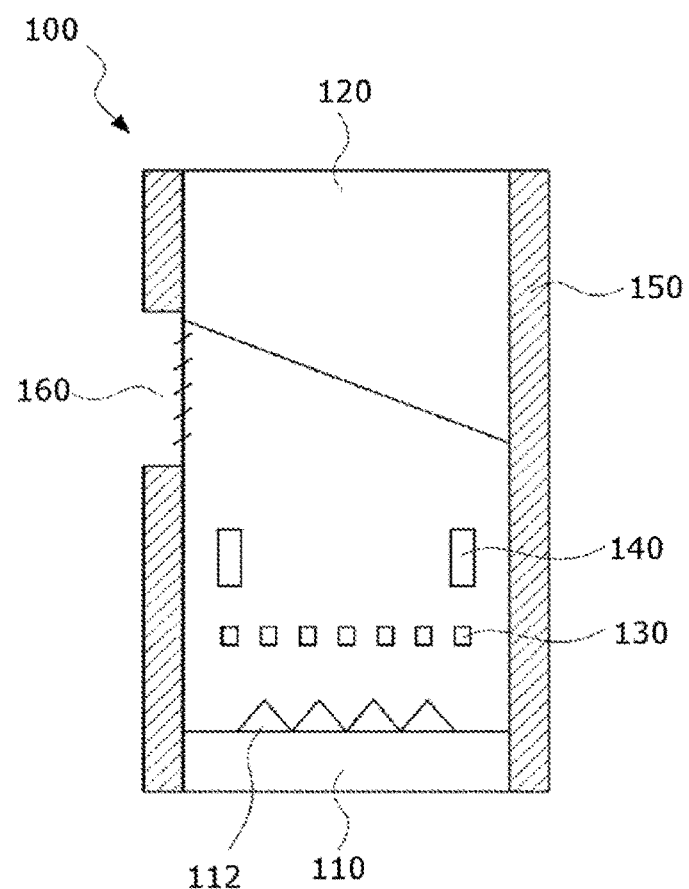
FIG. 2 is a sectional view illustrating an example of an X-ray source of FIG. 1.

FIG. 2 is a sectional view illustrating an example of the X-ray source.

Referring to FIG. 2, the X-ray source 100 may include: a cathode electrode 110 formed with a nanostructure 112; an anode electrode 120 facing the cathode electrode 110 with the nanostructure 112 being disposed therebetween; and a body 150 being in a tubular shape surrounding both the cathode electrode 110 and the anode electrode 120, with a window 160 being provided on a side of the body.

In other words, X-ray source 100 of the present invention is configured such that electrons that are emitted from the nanostructure 112 due to a voltage difference between the cathode electrode 110 and the anode electrode 120 are bombarded against the anode electrode 120, and thereby X-rays are emitted.

The cathode electrode 110 is provided at a first end inside the body 150, and is provided with the nanostructure 112 emitting electrons on a surface of the cathode electrode.

The cathode electrode 110 may be constituted by at least one of a silicon (Si) wafer, and a high-conductive metal or alloy; and the nanostructure 112 may be constituted by one of a carbon nanotube, carbon nanofibers, vitreous carbon, nanographite, a nanowire, a graphene, and a nanodiamond, wherein considering electron emission efficiency, it is preferred that a carbon nanotube is used for the nanostructure.

The carbon nanotube may be provided by being grown directly on an upper portion of the cathode electrode 110, or may be provided by plastic deformation after applying a carbon nanotube paste on the upper portion of the cathode electrode 110.

The anode electrode 120, which is provided at a second end inside the body 150 to face the cathode electrode 110 with the nanostructure 112 being disposed therebetween, preferably serves to produce a voltage difference between the anode electrode and the cathode electrode 110, and also serves as a target that emits X-rays by collision of the electrons emitted from the nanostructure 112.

To achieve this, the anode electrode 120 may provide an inclined surface that is configured to be close to the cathode electrode 110 as being away from the window 160, wherein the inclined surface serves as a target surface. However, without being limited thereto, various changes in the shape of the anode electrode 120 may be made according to a shape of an area that X-rays are emitted from.

The target surface of the anode electrode 120 may be made of a target material constituted by tungsten (W), copper (Cu), molybdenum (Mo), cobalt (Co), chromium (Cr), iron (Fe), silver (Ag), tantalum (Ta), or yttrium (Y), which generate X-rays by collision of the electrons. Alternatively, the anode electrode 120 itself may be made of a target material constituted by tungsten (W), copper (Cu), molybdenum (Mo), cobalt (Co), chromium (Cr), iron (Fe), silver (Ag), tantalum (Ta), or yttrium (Y).

Further, it is preferred that the X-ray source 100 is configured to be a three electrode structure by adding a gate electrode 130 between the cathode electrode 110 and the anode electrode 120, or is configured to be a four electrode structure by adding at least one focusing electrode 140 between the gate electrode 130 and the anode electrode 120.

The gate electrode 130, which emits electrons from the nanostructure 112 by using a predetermined voltage and also controls the amount of electron emission, may be in the form of a meshed metal grid.

The focusing electrode 140 serves to focus the electrons emitted from the nanostructure 112, which is similar to an optical lens for focusing light being incident onto a predetermined surface or a predetermined medium in the optical system. For example, the focusing electrode 140 may be in a ring shape, wherein an inner surface of the focusing electrode 140 may be made a metal material constituted by one of Kovar, stainless steel, aluminum (Al), and tungsten (W); and an outer surface of the focusing electrode may be made of an insulating material constituted by one of alumina ($Al_2O_3$), glass, and tungsten oxide ($WO_3$). However, without being limited thereto, the shape and material of the focusing electrode 140 may be appropriately determined by those skilled in the art.

The body 150 forms an external appearance of the X-ray source 100, and is in a tubular shape provided with the window 160 at a portion of a side surface of the body for allowing X-rays emitted from the anode electrode 120 to be irradiated outside. The body 150 defines a vacuum area separated from the outside by surrounding outer surfaces of the cathode electrode 110, the anode electrode 120, the gate electrode 130, and the focusing electrode 140.

For example, the body 150 may be made of an insulating material, such as glass or silicon, and thereby the body 150 serves to primarily insulate the X-ray source 100. Further, the window 160 may be constituted by one of beryllium (Be), aluminum (Al), magnesium (Mg), aluminum nitride (AlN), aluminum-beryllium alloy (AlBe), silicon oxide (SixOy), and titanium (Ti).

Meanwhile, the above description is an example of the X-ray source capable of being applied to the portable radiography device of the present invention, which is not intended to limit the portable radiography device of the present invention. In other words, the X-ray source 100 the portable radiography device of the present invention may be in the form of a conventional thermal electron source.

The control unit 200 serves to provide an image signal of a user control mode, which is about control of the X-ray source 100, to the projection unit 300, and to control the motion of the X-ray source 100 according to at least one user control mode selected by a user. To achieve this, the control unit 200 is a user operation unit for both selecting the user control mode, and performing radiography according to the selected control mode, and provides at least one control button and/or a jog dial.

The user control mode, as all of the control information on an output and a motion of the X-ray source, which the user can control according to the purpose of radiography, may be provided in the form of a predetermined kind and shape.

For example, the user control mode may include: a first control mode for selecting a patient, such as an adult or a child; a second control mode for selecting an object, such as a premolar, an incisor, or a molar; a third control mode for selecting a form of X-ray imaging, such as a film or a digital; a fourth control mode for selecting an applied voltage, namely, selecting a tube voltage; a fifth control mode for selecting an applied current, namely, selecting a tube current; and a sixth control mode for selecting X-ray exposure time. Further, these user control modes are displayed such that the user selects and changes the user control modes through the user control mode image. However, the user control mode may include all of the control information on the X-ray source, which is required for performing radiography according to a purpose, without being limited to the above mentioned modes.

The projection unit 300 serves to project the image signal of the user control mode of the control unit 200 to the outside as a predetermined user control mode image, and may be constituted by a projecting device by using one of liquid crystal display (LCD) projection, liquid crystal on silicon (LCOS) projection, and digital light processing (DLP) projection. However, without being limited thereto, those skilled in the art may appropriately select the projection unit as long as a projection technology and a projecting device allow an image to be projected by being applied to a miniaturized device. Further, the projection unit 300 receives the image signal of the user control mode wirelessly or by wire by being connected to the control unit 200.

LCD projection is a technology for a display device by using electro-optical properties of liquid crystal, in which light sources of red, green, and blue emitted from a lamp pass through a transmissive type LCD panel, and then are combined and create a single image through a polarizing prism, and thereby the image is projected on to a screen at an enlarged size.

Unlike LCD projection, the LCOS projection is a technology that uses how light is reflected against liquid crystal, in which after light coming out from one light source is split into its separate colors and is reflected against corresponding LCOS panels, each transmitted light is combined into a single image through a prism, and then the image is projected on to a screen at an enlarged size.

DLP projection is a technology that uses a digital mirror device (DMD) chip, in which light generated from a lamp passes through a color wheel, then is reflected against the DMD chip, and is projected on to a screen at an enlarged size. The DMD chip is a semiconductor optical switch that selectively reflects the light by micro mirrors switching more than thousands of times, wherein each aluminum alloy micro mirror, which is provided in a cell of static random access memory (SRAM) and has a size of 16 μm and rotates ±10° to an on or off state.

Figure 3:
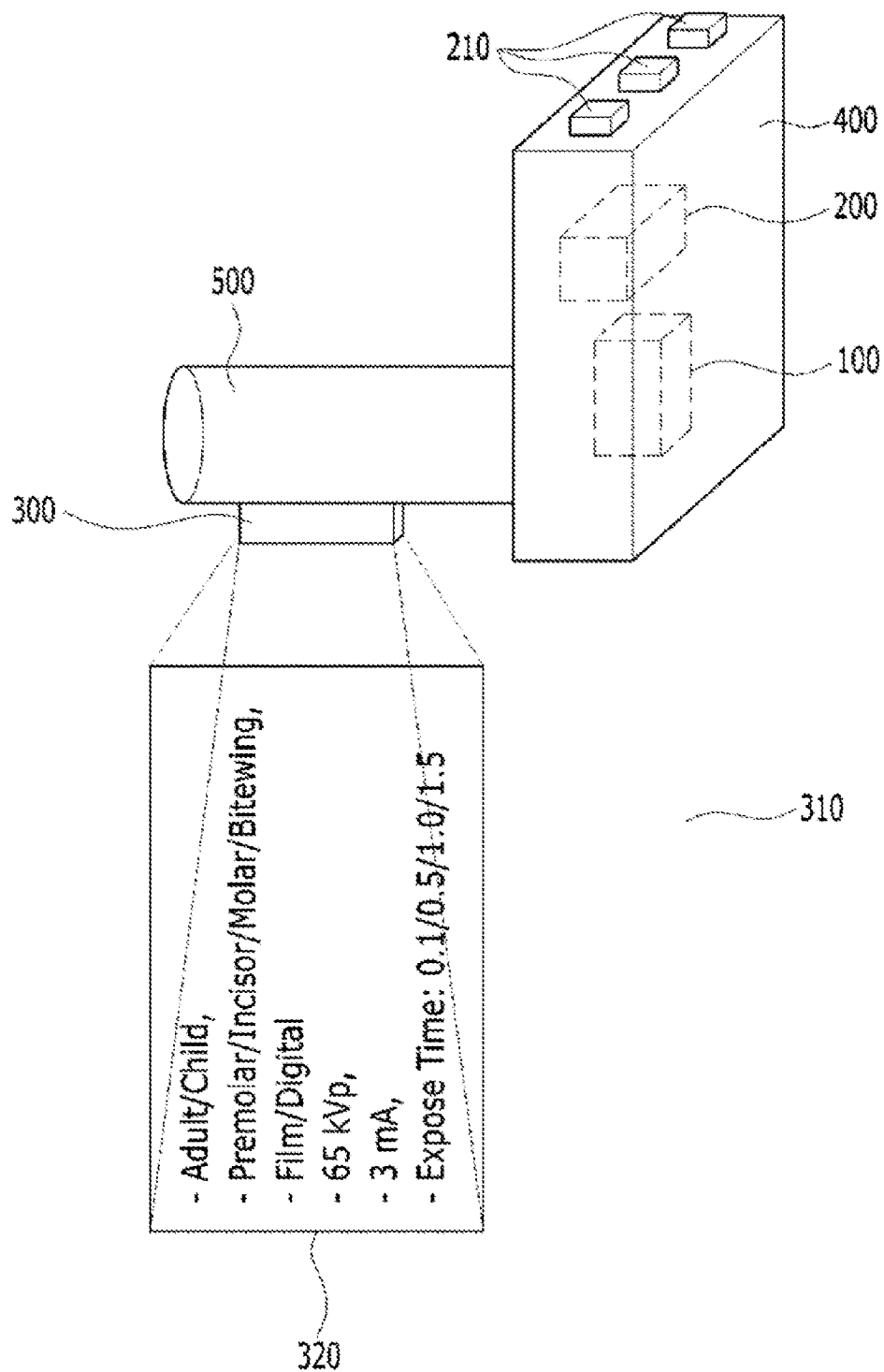
FIG. 3 is a schematic view illustrating a portable radiography device according to an embodiment of the present invention.
Figure 4:
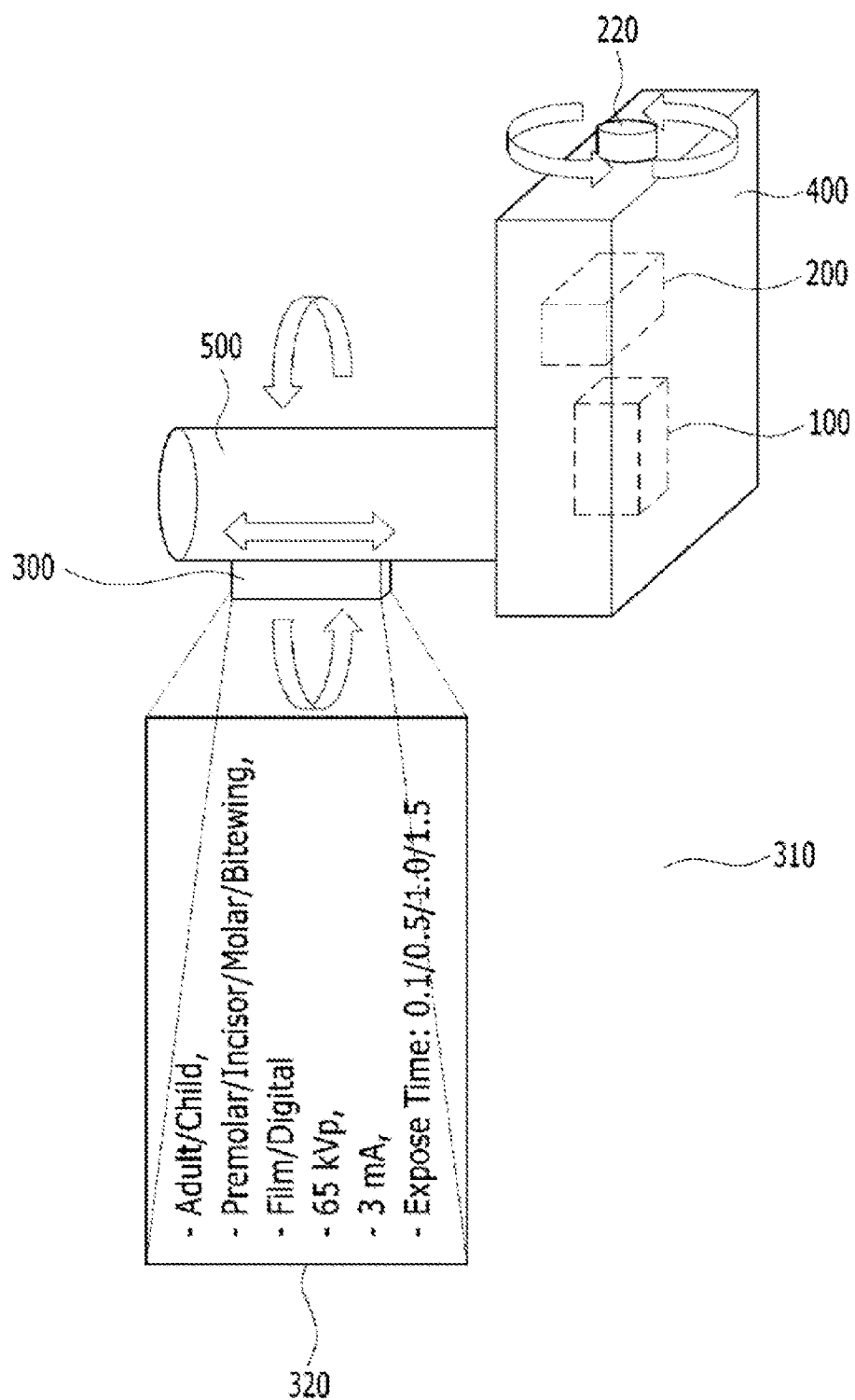
FIG. 4 is a schematic view illustrating a portable radiography device according to another embodiment of the present invention.

Hereinbelow, reference will be made to in detail to embodiments of the present invention, with reference to FIGS. 3 and 4. FIG. 3 is a schematic view illustrating a portable radiography device according to an embodiment of the present invention; and FIG. 4 is a schematic view illustrating a portable radiography device according to another embodiment of the present invention.

The portable radiography device of the present invention may include a housing 400 and an X-ray radiating guide 500, wherein the X-ray radiating guide 500 may be configured to be directly connected to a side of the housing 400 or to be connected to the housing 400 by means of a rotary unit (not shown) that is rotatably connected to the side of the housing 400. However, without being limited thereto, the X-ray radiating guide 500 may be integrally formed with the housing 400.

The housing 400 is provided with the control unit 200 for controlling the X-ray source 100 and the X-ray source 100 therein, and is preferably provided with a power unit (not shown) for supplying driving power to the X-ray source 100 and the control unit 200. The power unit may include a battery, and supplies battery power or outer power to the X-ray source 100 and the control unit 200.

Further, the housing 400, for example, may be provided with at least one control button 210 and/or a jog dial 220, as a user operation unit, at an upper portion of the housing. However, without being limited thereto, various changes in the shape and the location of the operation unit, which facilitate user operation, may be made.

The X-ray radiating guide 500 is provided with a collimator (not shown) for controlling an X-ray radiation direction and a dose of X-ray radiation, therein, so as to radiate X-rays generated from the X-ray source 100 in a desired size and direction, wherein the X-ray radiating guide is preferably in a tubular shape capable of adjusting length.

The projection unit 300 may be provided on a side of the housing 400 or the X-ray radiating guide 500, and it is preferred that the projection unit is detachably coupled to the housing 400 or the X-ray radiating guide 500.

For example, the projection unit 300 may rotate along with rotations of the X-ray radiating guide 500 by being coupled to a side of the X-ray radiating guide 500, or may be provided on a side of the X-ray radiating guide 500 to move or rotate along an outer surface of the X-ray radiating guide 500 separately from the X-ray radiating guide. For reference, detailed description of a mechanical structure for attachment, detachment, movement or rotation of the projection unit 300 will be skipped, as any structure well-known in art may be applied.

The portable radiography device according to the present invention is configured such that when the user, for example, manipulates at least one control button 210 or the jog dial 220, as a user operation unit, a user control mode image 320 is projected from the projection unit 300 to the outside, and the user control mode image 320 is displayed on a wall, a ceiling, or a screen 310.

Here, since the projection unit 300 is configured to be coupled or detachably coupled to a side of the housing 400 or the X-ray radiating guide 500, and configured to move or rotate along with the X-ray radiating guide 500 or separately therefrom, the user can manipulate the projection unit 300 so that the user control mode image can be projected and displayed at a desired location.

Thereby, while watching the user control mode image, the user can select and change a desired user control mode by using at least one control button 210 and/or the jog dial 220. Here, if necessary, the user can adjust a size or image quality of the user control mode image 320 by manipulating the control button 210 or the jog dial 220.

Further, upon completion of selection and change of the user control mode, the user can perform radiography according to the desired user control mode by using the control button 210 and/or the jog dial 220.

Unlike a conventional portable radiography device, which includes a display having a size of less than 3 inches, the portable radiography device of the present invention includes the projection unit 300, and thereby it is possible to improve visibility and legibility of the user control mode image 320 displaying various information on the user control mode.

Figure 5:
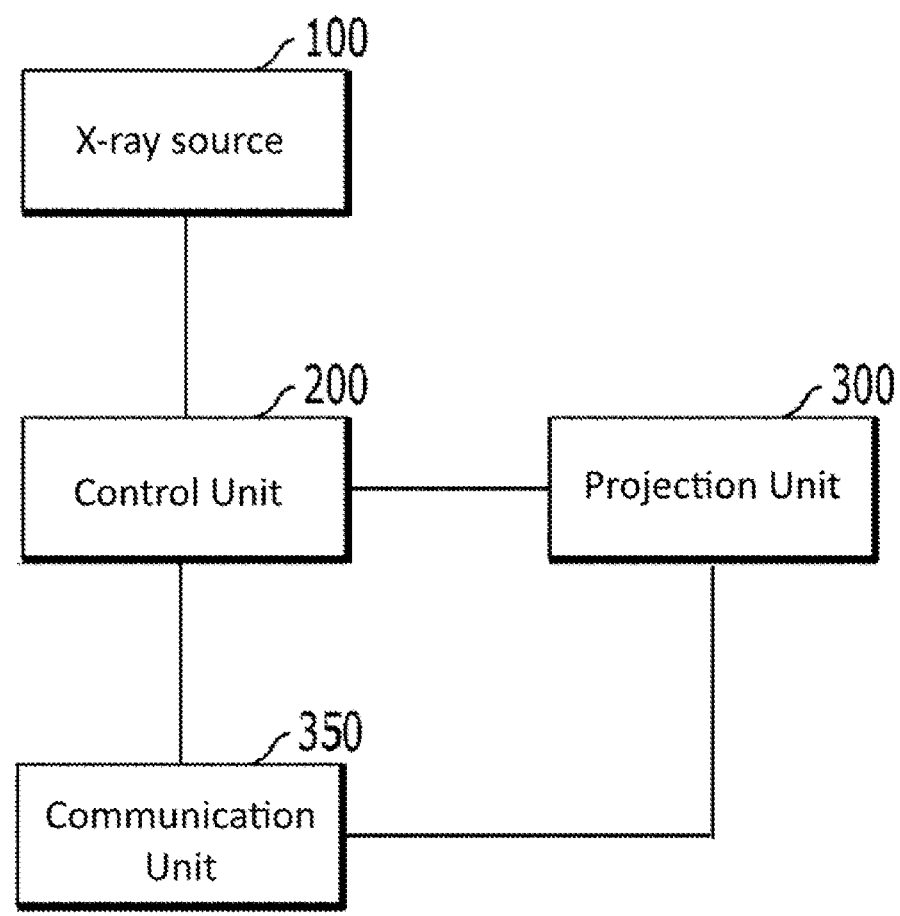
FIG. 5 is a block diagram illustrating a configuration of a portable radiography device according to further embodiment of the present invention.

Further, FIG. 5 is a block diagram illustrating a configuration of a portable radiography device according to further embodiment of the present invention.

Referring to FIG. 5, the portable radiography device according to the further embodiment of the present invention includes: the X-ray source 100; the control unit 200 for controlling the X-ray source 100; a communication unit 350 for receiving an image signal, as a radiographic outcome, by communicating with an X-ray sensor wirelessly or by wire; and the projection unit 300 for projecting at least one of the user control mode image of the control unit 200, and an intraoral radiograph by the image signal of the communication unit 350, to the outside.

As described above, the portable radiography device according to the further embodiment of the present invention is configured to project at least one of the user control mode image and the intraoral radiograph, to the outside through the projection unit 300, wherein the user control mode image is described hereinbefore.

Accordingly, reference will be made to projection of the intraoral radiograph to the outside, hereinbelow. When an intraoral image is radiographed, the X-ray sensor generates an electric signal, namely, an image signal, based on a dose of X-ray radiation according to a location, and then the image signal is transmitted wirelessly or by wire, to the communication unit 350 of the portable radiography device according to the further embodiment of the present invention.

Then, the image signal is converted into the intraoral radiograph in the control unit 200 or in the communication unit 350, and the projection unit 300 projects the intraoral radiograph to the outside. To achieve this, the control unit 200 or the communication unit 350 may be provided with an image processing unit having a predetermined algorithm and hardware for image processing, and if necessary, the portable radiography device according to the present invention may further include a memory unit so as to store a plurality of image signals or intraoral radiographs.

Here, user operation for selecting and projecting the intraoral radiograph may be performed through the above mentioned user operation unit and the control unit 200, and thereby the portable radiography device according to the further embodiment of the present invention is capable of projecting at least one of the user control mode image and the intraoral radiograph to the outside through the projection unit 300. Thus, it is possible for the user to diagnose and counsel a patient while watching the enlarged intraoral radiograph projected and displayed at a desired location.

For reference, if necessary, the portable radiography device according to the present invention is capable of sending at least one of a plurality of intraoral radiographs stored in the memory selected through the user operation unit, to an outer device, such as a computer, wirelessly or by wire. It is further understood by those skilled in the art that the foregoing description is a preferred embodiment of the disclosed device and that various changes and modifications may be made in the invention without departing from the spirit and scope thereof.

The invention claimed is:

1. A portable radiography device comprising:
   an X-ray source configured to generate X-rays;
   a projection unit rotatably and detachably attached to a housing of the portable radiography device and configured to project images at a predetermined area outside the portable radiography device, wherein the images includes i) a user control mode image including user control information for controlling the X-ray source, and ii) an intraoral radiograph obtained from an intraoral sensor; and
   a control unit configured to control the X-ray source for capturing the intraoral radiograph of a target object and the projection unit for projecting the captured intraoral radiograph at the predetermined area outside the portable radiograph device according to user inputs made based on the user control mode image, wherein the control unit includes an operation unit for receiving the user inputs,
   wherein the user control mode image is changed according to the user inputs.

2. The portable radiography device of claim 1, wherein the user control information includes information on at least one of a patient, an object, a form of X-ray imaging, a tube voltage, a tube current, and an X-ray exposure time.

3. The portable radiography device of claim 1, wherein the projection unit includes a projecting device for projecting images to the predetermined area outside the portable radiography device using one of liquid crystal display (LCD) projection, liquid crystal on silicon (LCOS) projection, and digital light processing (DLP) projection.

4. The portable radiography device of claim 1, further comprising:
   the housing for accommodating the X-ray source and the control unit therein; and
   an X-ray radiating guide provided in the housing and configured to guide radiating the X-rays,
   wherein the projection unit is rotatably and detachably attached on one side of the housing or the X-ray radiating guide, and the operation unit is provided on a side of the housing.

5. The portable radiography device of claim 4, wherein the X-ray radiating guide is rotatable relative to the housing.

6. The portable radiography device of claim 4, wherein the projection unit is removable and rotatable along one side of the X-ray radiating guide.

7. The portable radiography device of claim 4, wherein the operation unit includes at least one of a control button and a jog dial.

8. The portable radiography device of claim 1, further comprising:
 a communication unit configured to receive an image signal from the intraoral sensor wirelessly or by wire and provide the received image signal to the projection unit,
 wherein the projection unit generates the intraoral radiograph obtained from the image signal and project the intraoral radiograph to the predetermined area outside the portable radiography device.

* * * * *